(12) United States Patent
Polzius et al.

(10) Patent No.: US 9,204,865 B2
(45) Date of Patent: Dec. 8, 2015

(54) DEVICE FOR RECEIVING LIQUID SAMPLES

(75) Inventors: Rainer Polzius, Lübeck (DE); Thomas Wuske, Bad Malente (DE); Gero Vornbäumen, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 781 days.

(21) Appl. No.: 12/593,396

(22) PCT Filed: Jan. 16, 2008

(86) PCT No.: PCT/DE2008/000063
§ 371 (c)(1),
(2), (4) Date: Sep. 28, 2009

(87) PCT Pub. No.: WO2008/135001
PCT Pub. Date: Nov. 13, 2008

(65) Prior Publication Data
US 2010/0040506 A1 Feb. 18, 2010

(30) Foreign Application Priority Data
May 4, 2007 (DE) .......................... 10 2007 020 895

(51) Int. Cl.
| G01N 1/00 | (2006.01) |
| G01N 1/10 | (2006.01) |
| B01L 3/00 | (2006.01) |
| A61B 10/00 | (2006.01) |

(52) U.S. Cl.
CPC .................................. *A61B 10/0051* (2013.01)

(58) Field of Classification Search
CPC .............. G01N 1/00; G01N 1/10; B01L 3/00; B01L 3/0275; A61B 10/00
USPC ............................................................ 422/58
See application file for complete search history.

(56) References Cited

U.S. PATENT DOCUMENTS

| 3,967,127 A | * | 6/1976 | Rendina et al. .......... 250/441.11 |
| 5,260,031 A | | 11/1993 | Seymour |
| 5,613,491 A | * | 3/1997 | Kanner et al. ................ 600/369 |

(Continued)

FOREIGN PATENT DOCUMENTS

| DE | 197 48 331 C1 | 1/1999 |
| DE | 197 34 221 A1 | 2/1999 |

(Continued)

OTHER PUBLICATIONS

Arye, M. "Plastics 'poisoning world's seas'" BBC News, Science, Nature, 2006. 3 pages.*

*Primary Examiner* — Christine T Mui
(74) *Attorney, Agent, or Firm* — McGlew and Tuttle, P.C.

(57) ABSTRACT

A device for receiving liquid samples includes at least one sample carrier (1) for receiving the liquid sample, a sample carrier ejector (3) and a sample carrier holder (2) with a first guiding area and a second guiding area (4, 5) for guiding the sample carrier ejector (3). The first guiding area (4) has a tubular design and the second guiding area (5) has a groove-shaped design. The sample carrier ejector (3) has a geometry complementary to the first and second guiding areas (4, 5) and is axially displaceable within the sample carrier holder (2) such that the sample carrier (1) can be detached by the sample carrier ejector (3) from the sample carrier holder (2).

27 Claims, 2 Drawing Sheets

(56) References Cited

U.S. PATENT DOCUMENTS

| | | | |
|---|---|---|---|
| 6,440,087 B1 * | 8/2002 | Sangha | 600/582 |
| 6,489,172 B1 | 12/2002 | Bachand et al. | |
| 6,712,161 B1 * | 3/2004 | Dai | 175/58 |
| 2003/0224090 A1 * | 12/2003 | Pearce et al. | 426/89 |
| 2005/0256382 A1 | 11/2005 | Eisenmann et al. | |
| 2006/0002826 A1 * | 1/2006 | Lee et al. | 422/102 |
| 2006/0018800 A1 | 1/2006 | Slowey et al. | |
| 2006/0133956 A1 | 6/2006 | Hamanaka | |

FOREIGN PATENT DOCUMENTS

| | | | |
|---|---|---|---|
| DE | 198 09 930 A1 | 9/1999 | |
| DE | 102004022757 A1 | 12/2005 | |
| EP | 1 026 991 A1 | 8/2000 | |
| WO | 9812962 | 4/1998 | |
| WO | WO 03028889 A1 * | 4/2003 | B01L 3/00 |

* cited by examiner

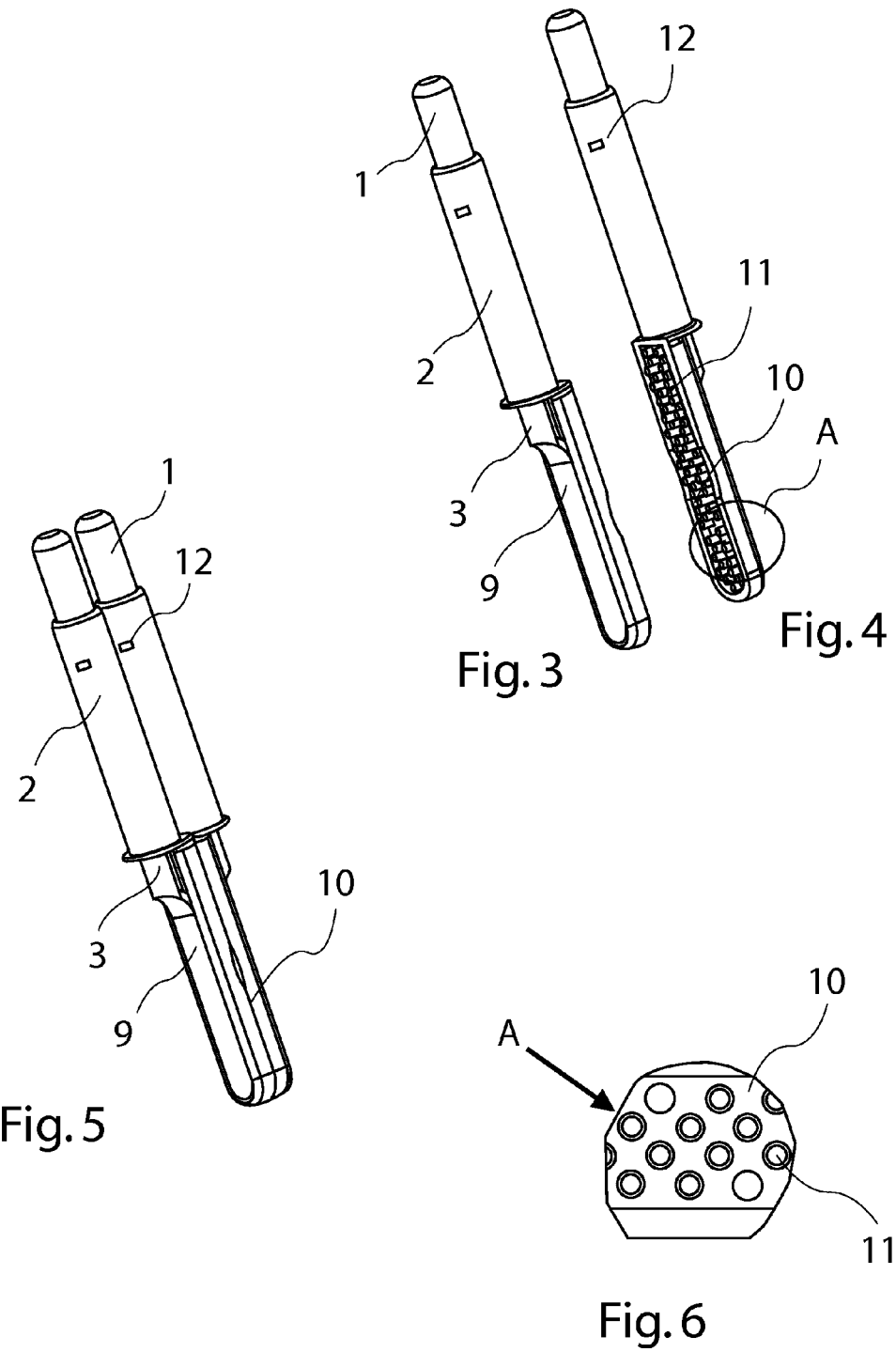

DEVICE FOR RECEIVING LIQUID SAMPLES

CROSS REFERENCE TO RELATED APPLICATIONS

This application is a United States National Phase application of International Application PCT/DE2008/000063 and claims the benefit of priority under 35 U.S.C. §119 of German Patent Application DE 10 2007 020 895.4 filed May 4, 2007, the entire contents of which are incorporated herein by reference.

FIELD OF THE INVENTION

The present invention pertains to a device for receiving liquid samples, especially saliva.

BACKGROUND OF THE INVENTION

Such devices are used, for example, by physicians to take a liquid sample with an absorbent material from a patient and to send the liquid sample taken to a laboratory, in which it can be analyzed for making a diagnosis. Saliva is a liquid sample whose significance has been increasing for some time. Saliva is analyzed to obtain diagnostic information, but also to detect substances that were administered or taken, especially medications or illegal drugs. Another use of the device is in the field of forensics, for example in the examinations of samples in connection with traffic offenses or testing for doping.

A device for receiving a liquid sample, which comprises essentially a tubular part and an elongated foam piece, is known from EP 10 269 91 A1. The foam piece is introduced into the tubular part and protrudes on at least one side of the tubular part for receiving the liquid sample. The device may also be designed to receive two liquid samples by the foam piece projecting at both ends of the tubular part. The entire device must be sent for an analysis of the liquid samples.

A device for receiving saliva for diagnostic purposes is known from DE 197 48 331 C1. The device comprises a porous part, which can be pressed out, receives liquid sample and is arranged within a container, which is closed on one side at one of its ends and can be displaced from this at another end, which end can be opened, wherein the container is preferably formed from a bellows. The saliva enters the bellows for being received and is taken up by the porous section. Only one saliva sample can be received at any one time.

DE 198 09 930 A1 discloses a device for receiving saliva samples, in which the saliva sample is taken up with a filter paper surface being held correspondingly. The entire device must likewise be sent for an analysis of the saliva sample. In addition, only one saliva sample can be taken up any one time.

U.S. Pat. No. 6,489,172 B1 discloses a device for receiving and releasing a saliva sample, in which an identical liquid sample can be divided in two containers, wherein a first quantity of liquid sample can be used for one examination and a second quantity of liquid sample is used to secure evidence. The examination of the first quantity of liquid sample takes place at the device, i.e., on site.

A device that makes it possible to divide a received liquid sample between two connected collection containers is described in US 2006/00188800 A1. A locally separated analysis or storage of the liquid samples in the two connected collection containers is not possible with this device.

DE 197 34 221 A1 discloses a sampling device with two housing parts displaceable relative to one another in the longitudinal direction, wherein a strip-shaped sample carrier is held by a pin fastened on the inside of one of the housing parts and by a leaf spring arranged on the second housing part.

SUMMARY OF THE INVENTION

The basic object of the present invention is to optimize a device for receiving liquid samples in terms of handling.

According to the invention, a device is provided for receiving liquid samples, the device comprising a sample carrier for receiving the liquid sample, a sample carrier ejector and a sample carrier holder. The sample carrier holder has a first guiding area and a second guiding area for guiding the sample carrier ejector. The first guiding area has a tubular design and the second guiding area has a groove-like design. The sample carrier ejector has a geometry complementary to the first and second guiding areas and is axially displaceable within the sample carrier holder such that the sample carrier can be detached by the sample carrier ejector from the sample carrier holder.

An essential advantage of the present invention compared to the state of the art is the simple hygienic separation of the sample carrier from the sample carrier holder for purposes of analyzing the liquid sample. The sample carrier preferably consists of a dimensionally stable material and is fixed by a holding pressure within the sample carrier holder. A pressure, which is higher than the holding pressure of the sample carrier within the sample carrier holder, can be generated by the sample carrier ejector by an axial displacement of the sample carrier ejector within the sample carrier holder. The sample carrier becomes detachable from the sample carrier holder as a result and, furthermore, a specific release of the sample carrier, for example, into a vessel, is made possible.

Using the device according to the present invention, the user has a hygienic process for taking a liquid sample from a test subject and for transporting same for further processing.

The device according to the present invention is designed in a preferred embodiment such that on a part of the sample carrier holder facing away from the sample carrier, the sample carrier holder has a coupling area, by means of which two sample carrier holders of identical design can be coupled with one another. This makes it possible to simultaneously receive two liquid samples or to store two separate liquid samples. Simultaneous analysis of two liquid samples is required in some countries, for example, for preparing an independent expert opinion after a drug test. A minimal volume of liquid samples is required for the reference analysis in some analysis processes. The holding capacity of a sample carrier may not possibly be sufficient in this connection. The necessary quantity of liquid sample can be increased of means of two sample carriers. The user can thus respond flexibly to the liquid sampling necessary in a particular case in a simple manner with the device according to the present invention.

In another embodiment of the device according to the present invention, the sample carrier may have a moisture indicator, which indicates the receipt of the liquid sample. The moisture indicator may be an indicator dye, which shows a change in color in the presence of moisture. A preferred indicator dye is a water-soluble food coloring. The moisture indicator may be preferably introduced into the material of the sample carrier.

The device for receiving liquid samples according to the present invention can be used to receive liquid samples for diagnostic analyses or identifications of DNA, RNA, antibodies, drugs, etc.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 is a simplified view of the device according to the present invention in a first lateral view;

FIG. 4 is a simplified view of the device according to the present invention in a second lateral view;

FIG. 5 is a simplified view of two devices according to the present invention, which are connected to one another; and FIG. 6 is a detail "A" of the device of FIG. 4 according to the present invention.

DESCRIPTION OF THE PREFERRED EMBODIMENTS

Figure 1:
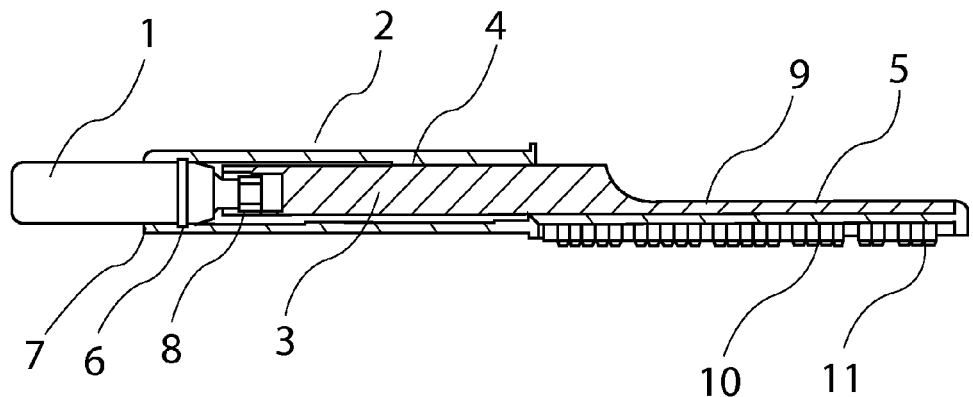
FIG. 1 is a simplified sectional view of the device according to the present invention.
Figure 2:
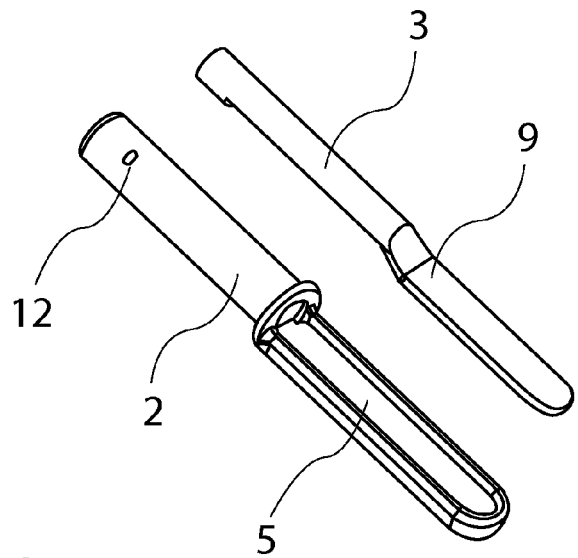
FIG. 2 is a simplified view of the sample carrier holder and sample carrier ejector.

Referring to the drawings in particular, FIG. 1 shows the device according to the present invention for receiving a liquid sample, which comprises a sample carrier 1 for receiving the liquid sample, a sample carrier holder 2 and a sample carrier ejector 3. As is shown in FIG. 2, the sample carrier holder 2 and the sample carrier ejector 3 are of a one-part design each. The sample carrier ejector 3 is axially displaceable at least partially within the sample carrier holder 2. The sample carrier holder 2 has two guiding areas, in which the sample carrier ejector 3 is guided during an axial displacement. A first guiding area 4 has a tubular design and a second guiding area 5 has a groove-like design with a lateral circumferential edge. The sample carrier ejector 3 has a shape correspondingly complementary to those of the first and second guiding areas 4, 5 of the sample carrier holder 2. In an assembled state of the sample carrier holder 2 and the sample carrier ejector 3, a piston-like first part of the sample carrier ejector 3 is guided within the first guiding area 4 of the sample carrier holder 2, whereas a flat second part of the sample carrier ejector 3 is guided within the second guiding area 5 of the sample carrier holder 2.

The first guiding area 4 of the sample carrier holder 2 has, furthermore, a receiving area 7 for receiving an essentially cylindrical sample carrier 1. The sample carrier 1 preferably consists of a dimensionally stable material. The sample carrier 1 is preferably pressed into the sample carrier holder 2 and fixed in the receiving area 7 by the holding pressure generated thereby within the sample carrier holder 2. The area of the sample carrier 1 engaging the receiving area 7 of the sample carrier holder 2 may be preferably of a conical shape for satisfactory fixation of the sample carrier 1 in the sample carrier holder 2.

The receiving area 7 is provided, furthermore, with an undercut 6, which acts as a stop for the sample carrier ejector 3. A defined range of displacement of the sample carrier ejector 3 is thus guaranteed. The part of the piston-shaped sample carrier ejector 3 cooperating with the sample carrier 1 preferably has a tubular design, and the internal diameter of the tubular part of the sample carrier ejector 3 is selected to be such that this can be caused to engage the sample carrier 1. At least one part of the part of the sample carrier 1 protruding into the sample carrier holder 2 has a shoulder with a smaller diameter.

The flat second part of the sample carrier ejector 3 (FIG. 3) has a grip area 9, by means of which the sample carrier holder 2 can be held, on the one hand, and, on the other hand, the axial displacement of the sample carrier ejector 3 within the sample carrier holder 2 is effected manually. Due to the axial displacement of the sample carrier ejector 3 within the sample carrier holder 2, a pressure can be generated by the sample carrier ejector 3 on the sample carrier 1, which pressure is higher than the holding pressure of the sample carrier 1 within the sample carrier holder 2. The sample carrier ejector 3 is preferably provided, furthermore, with a grip surface for a thumb. By pressing this grip surface with the thumb, the sample carrier ejector 3 can be displaced within the sample carrier holder 2 in the direction of the sample carrier 1 and the sample carrier 1 can be moved out of the sample carrier holder 2 against the resistance of the holding pressure. Due to this embodiment of the device according to the present invention, the user can displace the sample carrier ejector 3 in the direction of the sample carrier 1 with one hand, so that the sample carrier 1 can be detached from the sample carrier holder 2 and introduced in a specific manner, for example, into a separate vessel for analysis or storage.

The sample carrier 1 is equipped with a moisture indicator 8, which indicates the receipt of the liquid sample. The moisture indicator 8 is preferably introduced into the material of the sample carrier 1. The moisture indicator 8 may be essentially an indicator dye, which shows a color change in the presence of moisture. The indicator dye is preferably a water-soluble food coloring. The sample carrier 1 is preferably prepared by means of a sintering process. The food coloring particles may advantageously be introduced into the material of the sample carrier 1 during the sintering process. However, the moisture indicator 8 may also have a ring-shaped design in an embodiment variant, not shown, and be preferably applied to the part of the sample carrier 1 with the smaller diameter. If a liquid sample is admitted to the sample carrier 1, the color of the moisture indicator 8 changes in case of a sufficient quantity of liquid sample due to the colored particles introduced into the sample carrier 1 and present in the attachable moisture indicator 8. The change in color signals to the user a sufficient quantity of liquid sample and hence the conclusion of the liquid sampling. The receiving area 7 of the sample carrier holder 2 is made of an optically transparent material, which permits visual checking of the sample carrier 1 used and, moreover, makes visible a color change of the moisture indicator 8 in case of sufficient wetting by the liquid sample. In addition, a window 12, through which the particular state of the moisture indicator 8 can be recognized, may be provided in the outer surface of the sample carrier holder 2. In one embodiment variant, not shown, the window 12 may be provided with a lens for better visibility of the moisture indicator 8.

As is shown in FIG. 4, the sample carrier holder 2 has a coupling area 10, by means of which two sample carrier holders 2 can be coupled with one another, on the side facing away from the second guiding area 5. This makes it possible to connect two sample carrier holders 2 of identical design to one another in a simple manner to form a liquid sampling system and to detach the sample carrier holder 2 in a likewise simple manner subsequent to a performed liquid sampling. The device according to the present invention thus offers the possibility of simultaneously receiving two separate quantities of liquid sample, which can subsequently be passed on separately for analysis or storage. A simplified view of two sample carrier holders 2 connected to one another is shown in FIG. 5.

FIG. 6 shows an enlarged detail "A" of the coupling area 10 shown in FIG. 4. The coupling area 10 is provided with coupling means, which are designed as uniform coupling pins 11 and are arranged in a two-dimensional periodic pattern, an intermediate space each having at least the diameter of the coupling pins 11 being provided each between the coupling pins 11.

While specific embodiments of the invention have been described in detail to illustrate the application of the principles of the invention, it will be understood that the invention may be embodied otherwise without departing from such principles.

The invention claimed is:

1. A device for receiving a liquid sample, the device comprising:
   a sample carrier formed of a dimensionally stable absorbent material for receiving the liquid sample;
   a sample carrier ejector; and
   a sample carrier holder with a first guiding area and a second guiding area for guiding the sample carrier ejector, wherein the first guiding area has a tubular design and the second guiding area has a groove-like design with an open longitudinal side, and the sample carrier ejector has a geometry complementary to the first and second guiding areas and said carrier ejector is axially displaceable within the sample carrier holder such that the sample carrier can be detached by the sample carrier ejector from the sample carrier holder and from the sample carrier ejector.

2. A device in accordance with claim 1, wherein the first guiding area has a receiving area for receiving the sample carrier, wherein the sample carrier has a part engaging the receiving area, said part having a conical shape, said second guiding area being spaced from said sample carrier.

3. A device in accordance with claim 1, wherein the receiving area has an undercut.

4. A device in accordance with claim 2, wherein at least the receiving area of the sample carrier holder is made of an optically transparent material.

5. A device in accordance with claim 1, wherein the sample carrier holder and the sample carrier ejector are each of a one-part design.

6. A device in accordance with claim 1, wherein the sample carrier is essentially cylindrical, wherein the sample carrier has a part cooperating with the sample carrier ejector, said part of said sample carrier having a shoulder with a smaller diameter.

7. A device in accordance with claim 6, wherein the sample carrier has a moisture indicator reacting with a liquid sample.

8. A device in accordance with claim 7, wherein the moisture indicator has a ring-shaped design and can be applied to the part of the sample carrier with the smaller diameter.

9. A device in accordance with claim 7, wherein the moisture indicator is introduced into a material of the sample carrier.

10. A device in accordance with claim 7, wherein the moisture indicator is essentially an indicator dye, which shows a color change in the presence of moisture.

11. A device in accordance with claim 10, wherein the indicator dye is a water-soluble food coloring.

12. A device in accordance with claim 1, wherein the sample carrier ejector has a grip area, by means of which the sample carrier ejector can be held and manually displaced by an operator through said open longitudinal side of said sample carrier holder.

13. A device in accordance with claim 1, wherein on the side facing away from the second guiding area the sample carrier holder has a coupling area, by means of which two sample carrier holders can be coupled with one another.

14. A device in accordance with claim 13, wherein the coupling area has coupling pins arranged in a two-dimensional periodic pattern, wherein an intermediate space with at least the diameter of a coupling pins is provided between the coupling pins.

15. A device for receiving a liquid sample, the device comprising:
   a sample carrier formed of a dimensionally stable absorbent material for receiving the liquid sample;
   a sample carrier ejector having a first shaped portion and a pressing portion for being pressed; and
   a sample carrier holder with a first ejector receiving area for guiding the sample carrier ejector and a second ejector receiving area for guiding the sample carrier ejector, said sample carrier being arranged in said first ejector receiving area, said first ejector receiving area having a geometry complementary to the first shaped portion, said second ejector receiving area being spaced from said sample carrier and having a groove shape geometry with an open longitudinal side for guiding said pressing portion while providing access to said pressing portion through said open longitudinal side, said sample carrier ejector being axially displaceable within the sample carrier holder for pressing the sample carrier out from the sample carrier holder and away from said sample carrier ejector.

16. A device in accordance with claim 15, wherein the sample carrier ejector pressing portion includes a grip area for holding and manually displacing said sample carrier ejector by an operator through said open longitudinal side of said sample carrier holder.

17. A device in accordance with claim 15, wherein said sample carrier holder has a coupling area with structure for coupling the sample carrier holder to another said sample carrier holder.

18. A sampling device for receiving and discharging a liquid sample, the device comprising:
   a sample carrier formed of a dimensionally stable absorbent material capable of receiving the liquid sample;
   a holder having a tubular shape and defining a first guiding area inside said tubular shape, said tubular shape having first and second open ends, said first opened end and said sample carrier being formed and shaped to have said sample carrier connect to said first opened end, said sample carrier being slidable out of said first opened end, said holder including an open groove section connected to said second opened end, said open groove section defining a second guiding area, and having a open longitudinal side;
   an ejector with a first part arranged in said first guiding area, and a second part arranged in said second guiding area, said ejector being slideably arranged in said first and second guiding areas to have said first part push said sample carrier out of said first end of said holder and disconnect said sample carrier from said holder and said ejector when said second part of said ejector is operated by a user to slide toward said first end with said ejector remaining in said holder, said open longitudinal side providing access by an operator to move said ejector in said holder.

19. A sampling device in accordance with claim 18, further comprising:
   a coupling area arranged on said holder and shaped to be directly attachable to a coupling area on another holder similar to said holder;

said first and second ends of said holder being on diametrically opposite ends of said holder.

20. A sampling device in accordance with claim 18, further comprising:
    another sample carrier connected to another holder with another ejector;
    coupling areas on said holder and said another holder, said coupling areas directly connecting said holder and said another holder adjacent to each other to arrange both sample carriers adjacent to each other for simultaneously receiving of the liquid sample.

21. A sampling device in accordance with claim 18, wherein:
    said first opened end and said sample carrier are formed and shaped to have one of said sample carrier and said first opened end deform when said sample carrier is inserted into said first opened end, the deformation holding said sample carrier in said first opened end by a holding pressure;
    said ejector selectively applying pressure from the operator to said sample carrier to overcome said holding pressure and to disconnect said sample carrier from said holder.

22. A sampling device in accordance with claim 18, wherein:
    said sample carrier and said ejector are separate and are not directly fixed to each other.

23. A device in accordance with claim 1, wherein:
    said sample carrier holder and said sample carrier are formed and shaped to have one of said sample carrier and said sample carrier holder deform when said sample carrier is inserted into said sample carrier holder, the deformation holding said sample carrier in said sample carrier holder by a holding pressure;
    said sample carrier ejector selectively applies pressure from the operator to said sample carrier to overcome said holding pressure and to disconnect said sample carrier from said sample carrier holder.

24. A device in accordance with claim 1, wherein:
    said sample carrier and said sample carrier ejector are separate and are not directly fixed to each other.

25. A device in accordance with claim 15, wherein:
    said sample carrier holder and said sample carrier are formed and shaped to have one of said sample carrier and said sample carrier holder deform when said sample carrier is inserted into said sample carrier holder, the deformation holding said sample carrier in said sample carrier holder by a holding pressure;
    said sample carrier ejector selectively applies pressure from the operator to said sample carrier to overcome said holding pressure and to disconnect said sample carrier from said sample carrier holder.

26. A sampling device in accordance with claim 15, wherein:
    said sample carrier and said sample carrier ejector are separate and are not directly fixed to each other.

27. A sampling device in accordance with claim 18, wherein:
    said sample carrier is press fit into said holder to generate a holding pressure that fixes said carrier into said first open end of said holder.

* * * * *